United States Patent [19]

Burdette et al.

[11] 4,401,837

[45] Aug. 30, 1983

[54] EXO-TETRAHYDROTRICYCLOPENTADIENE, A HIGH DENSITY LIQUID FUEL

[75] Inventors: George W. Burdette, Ridgecrest, Calif.; Abraham I. Schneider, Philadelphia, Pa.

[73] Assignee: The United States of America as represented by the Secretary of the Navy, Washington, D.C.

[21] Appl. No.: 155,879

[22] Filed: Jun. 2, 1980

[51] Int. Cl.$^3$ .................... C07C 5/22; C07C 13/615; C10L 1/16
[52] U.S. Cl. .................... 585/253; 149/109.4; 585/21; 585/14
[58] Field of Search ............. 149/109.4; 585/21, 14, 585/253

[56] References Cited

U.S. PATENT DOCUMENTS

| | | | |
|---|---|---|---|
| 3,002,829 | 10/1961 | Kolfenback | 149/109.4 |
| 3,165,887 | 1/1965 | Koch | 149/109.4 |
| 3,326,992 | 6/1967 | Muller | 149/109.4 |
| 3,377,398 | 4/1968 | Zoche | 149/109.4 |
| 3,701,812 | 10/1972 | Gebhart et al. | 149/109.4 |
| 4,059,644 | 11/1977 | Cannell | 149/109.4 |
| 4,222,800 | 9/1980 | Myers, Jr. et al. | 585/14 |
| 4,286,109 | 8/1981 | Norton et al. | 585/14 |
| 4,320,238 | 3/1982 | Norton et al. | 585/14 |

*Primary Examiner*—Henry R. Jiles
*Assistant Examiner*—Robert C. Whittenbaugh
*Attorney, Agent, or Firm*—R. F. Beers; W. Thom Skeer

[57] ABSTRACT

A high density fuel for airbreathing or bi-propellant engines consisting of exo-tetrahydrotricyclopentadiene (EXO-THTC) alone and in mixtures with other high density fuels. Processes for their preparation are also disclosed.

3 Claims, No Drawings

EXO-TETRAHYDROTRICYCLOPENTADIENE, A HIGH DENSITY LIQUID FUEL

BACKGROUND OF THE INVENTION

This invention relates to an improved high density liquid airbreather and bi-propellant engine fuels. Further, it also relates to an improved high density liquid airbreather fuel alone and with mixtures of other high density liquid airbreather fuels that allows a customizing ability to prepare such fuels for certain end uses.

High density fuels for airbreathing engines are necessary for use in military jet aircraft and missiles in order to obtain greater efficiency. Greater efficiency is an ever sought after goal for such end uses in order to obtain greater range through higher density, that is, more energy per unit fuel volume. Further, a higher flash point for added safety to avoid premature ignition and, improved physical and chemical properties are also sought after goals.

Several high density fuels are known in the art. With perhaps Cannell, U.S. Pat. No. 4,059,644, being one recent example of a process for preparing such fuels and a fuel product by such process. Cannell shows a method for preparing high density fuels by oligomerization of a mixture of cyclopentadiene dimer and methylcyclopentadiene dimer to their co-trimer followed by hydrogenation of the oligomerization product. And, even though many high density fuels are available, even greater density fuels with higher flash points for safer use are sought to yield a reliable high density fuel with greater range in a safe manner. Moreover, other existing fuels that may be classed as competitive are either considerably lower in volumetric heating value (related to missile range) or are considerably more expensive.

SUMMARY OF THE INVENTION

A new and improved high density fuel for airbreathing engines and a process for preparing it are illustrated in the present invention. In accordance with this invention, a new and improved high density fuel for airbreathing engines and a process for preparing it, consisting of pure exo-tetrahydrotricyclopentadiene (EXO-THTC) alone and in combination with mixtures of other high density fuels are illustrated.

OBJECTS OF THE INVENTION

It is an object of this invention to provide a new and improved high density fuel for airbreathing engines consisting of EXO-THTC.

Another object of this invention provides new and improved high density fuel for airbreathing engines consisting of EXO-THTC and in combination with mixtures of other high density fuels.

Still another object of this invention provides processes for preparing the new and improved high density fuel for airbreathing engines.

These and other objects are accomplished in the present invention by providing new and improved high density fuels consisting of pure EXO-THTC alone and in combination with other high density fuels and, processes for preparing said new and improved high density fuels.

DESCRIPTION OF THE PREFERRED EMBODIMENT

The starting materials for preparing the high density fuels of this invention are the readily available endo, and exo, isomers of tetrahydrotricyclopentadiene, melting point 48.9° C., made by distilling the trimer fraction from the product of heating dicyclopentadiene in a closed system at about 170° C., followed by catalytic hydrogenation of the reaction mixture. These starting compounds are readily available as products from cracking or pyrolysis of petroleum distillates, naphthas, kerosenes, etc.

EXAMPLE 1

Dicyclopentadiene ($C_{10}H_{12}$—three rings) is added to a closed system and heated to a temperature of 170° C. Tricyclopentadiene, tetracyclopentadiene and pentacyclopentadiene are obtained as the reaction mixture. Analyses show tricyclopentadiene having five rings and a $C_{15}H_{18}$ structure, tetracyclopentadiene having seven rings and a $C_{20}H_{24}$ structure and pentacyclopentadiene having nine rings and a $C_{25}H_{30}$ structure.

The reaction mixture is then hydrogenated in the presence of a nickel-on-kieselguhr catalyst and tetrahydrotricyclopentadiene, tetrahydrotetracyclopentadiene and tetrahydropentacyclopentadiene are obtained. Analyses show tetrahydrotricyclopentadiene having a structure of $C_{15}H_{22}$, a mass of 202.33 and a melting point of 49° C.; tetrahydrotetracyclopentadiene having a structure of $C_{20}H_{28}$, a mass of 268.43 and a melting point of approximately 205° C.; and tetrahydropentacyclopentadiene having a structure of $C_{25}H_{34}$ and a mass of 334.53. The trimer product yield is maximized by adjusting temperature and heating time during cracking and condensing. The trimer fraction product, tetrahydrotricyclopentadiene is isomerized by treatment with aluminum chloride at a temperature of from 0° C. to 20° C. in a methylene chloride solvent to form exo-tetrahydrotricyclopentadiene having the following properties: formula—$C_{15}H_{22}$; density—1.0376; flash point—121° C.; viscosity (cp)—37 at 20° C., 97 at 0° C., and 510 at −20° C.; freezing point—below −40° C.; ΔHc, net, Btu/gal.—155,522, ΔHc, net, Btu/lb.—18,110, %ΔHc (Btu/gal.) (above JP-5)—21 and an estimated cost/lb. (car lots) $3.00.

EXAMPLE 2

The exo-tetrahydrotricyclopentadiene product as prepared in Example 1 is mixed with an exo-tetrahydrodicyclopentadiene in a sixty to forty weight percent ratio. The following properties were obtained upon analysis of this mixture: formula—60 weight % $C_{15}H_{22}$, 40 weight % $C_{10}H_{16}$; density—0.996; flash point—above 60° C.; viscosity (cp)—10 at 20° C., 40 at −18° C. and 170 at −40° C.; freezing point—below −40° C.; ΔHc, net, Btu/gal. 150,600; ΔHc, net, Btu/lb. 18,090; %ΔHc, Btu/gal. (above JP-5) 17 and cost/lb. (car lots) of about $3.00.

EXAMPLE 3

The product of Examples 1 and 2 are compared in this example with JP-5 ($C_{10}H_{19}$), exo-tetrahydrodicyclopentadiene (EXO-THDC) ($C_{10}H_{16}$), and RJ-5 ($C_{14}H_{18.4}$). The results upon analyses show the following properties:

|  | JP-5 | EXO—THDC | RJ-5 |
| --- | --- | --- | --- |
| Formula | $C_{10}H_{19}$ | $C_{10}H_{16}$ | $C_{14}H_{18.4}$ |
| Density | 0.788–0.845 at 20° C. | 0.936 at 16° C. | 1.08 at 16° C. |
| Flash Point (°C.) | 60 (min) | 56 | 116 |

|  | JP-5 | EXO—THDC | RJ-5 |
|---|---|---|---|
| Viscosity (cp) | 14 at −40° C. | 17 at −40° C. | 2000 at −40° C. |
| Freezing Point (°C.) | −46 (max) | below −40 | above −40 |
| Cost/lb. ($) | 0.20 | 3 | 15 |
| $\Delta$Hc (net) (Btu/gal.) | 125,000 | 141,700 | 161,000 |
| % $\Delta$Hc (Btu/gal.) (above JP-5) | 0 | 12 | 23 |

The pure EXO-THTC and with mixtures illustrate excellent fuels for missiles and aircraft that use airbreathing engines as a means of propulsion. Further, EXO-THTC is a highly promising, yet inexpensive bi-propellant fuel for rocket propulsion, having a high specific impulse and high propellant density wherein the stoichiometry for combustion is to CO and $H_2O$.

It is noted from the examples that pure EXO-THTC yields the highest heating value possible with the exception of RJ-5 wherein the cost is about five times as great for substantially equivalent heating value. The "exo" fuels exhibit significantly higher heating values and thus greater range capability than the JP-5 standard heretofore and at a reasonable cost of about one dollar per pound in production quantities.

Other mixtures of fuels with EXO-THTC are considered within the purview of applicants invention and the invention is not considered to be limited to the specific examples presented.

What is claimed is:

1. A process for the preparation of a high density fuel for airbreathing engines consisting of exotetrahydrotricyclopentadiene (EXO-THTC) $C_{15}H_{22}$, which comprises:
   distilling the trimer fraction of the reaction mixture from the product of heating dicyclopentadiene in a closed system at a temperature of about 165° C. to about 175° C. and for a period of time sufficient to maximize said trimer yield,
   hydrogenating said trimer fraction in the presence of nickel-on-Kieselguhr catalyst to form tetrahydrotricyclopentadiene,
   isomerizing said tetrahydrotricyclopentadiene by treatment with aluminum chloride at a temperature of from 0° C. to 20° C. in a methylene chloride solvent to form exo-tetrahydrotricyclopentadiene.

2. A process as in claim 1 wherein said hydrogenation is carried out at a temperature and period of time sufficient to maximize said tetrahydrotricyclopentadiene yield.

3. A process as in claim 1 wherein about 40 to about 60 weight percent of said EXO-THTC is replaced with a like amount of exo-tetrahydrodicyclopentadiene.

* * * * *